United States Patent [19]

Kleefeld et al.

[11] Patent Number: 5,095,029
[45] Date of Patent: Mar. 10, 1992

[54] FUNGICIDAL 1,3,5-TRIARYL-2-PYRAZOLINES

[75] Inventors: Gerd Kleefeld; Stefan Dutzmann, both of Duesseldorf, Fed. Rep. of Germany

[73] Assignee: Bayer Aktiengesellschaft, Leverkusen, Fed. Rep. of Germany

[21] Appl. No.: 546,143

[22] Filed: Jun. 28, 1990

[30] Foreign Application Priority Data

Jul. 20, 1989 [DE] Fed. Rep. of Germany ....... 3924112

[51] Int. Cl.$^5$ ............................................. A01N 43/56
[52] U.S. Cl. .................................... 514/403; 548/379
[58] Field of Search ........................ 514/403; 548/379

[56] References Cited

FOREIGN PATENT DOCUMENTS 0267869 7/1982 European Pat. Off. .

OTHER PUBLICATIONS

Fahmy, A. M., "Synthesis of Some New β-Lactams . . . ", Indian Journal of Chemistry, 1987, vol. 26B, pp. 884–887.
Asaad, F. M., "New Pyrazolines and Pyrazoles . . . ", Egypt. J. Chem., vol. 25(3), 1982, pp. 293–300.
Roda, K. P. et al., "Studies on 2-Pyrazolines: Part-I: . . . ", J. Inst. Chemists (India), 1989, vol. 61, pp. 51–52.
Yulog, Nuran et al., "Antifungal Activities of Some . . . ", ACTA Pharmaceutica Turcica, 1989, vol. 31, pp. 111–114.
Latif, N. et al., "Newer Carbamates from Vanillin", Indian Journal of Chemistry, 1980, vol. 19B, pp. 301–304.
Chemical Abstracts 112: 178777C abstracting: RODA et al. "Studies on 2-pyrazolines. Part I. . ." J. Inst. Chem. vol. 61(2), pp. 51–2, 1989.
Chemical Abstracts 112: 52075d abstracting: Yulug et al. "Antifungal activities of some 1,3,5-triphenyl-2-pyrazoline . . ." Acta Pharm. Turc. vol. 31(3), pp. 111–114, 1989.
Chemical Abstracts 111: 778985 abstracting: Fahmy et al. "Synthesis of some new p-lactans . . ." Rev. Roum. Chim. vol. 33(7), pp. 755–61, 1988.
Chemical Abstracts 109: 125684b abstracting: Bilgin et al., "Some 1,3,5-Triphenyl-2-Pyrazoline Derivatives", Hace Hepe Univ. Eczacilik Fak. Derg., vol. 7(2), pp. 73–80, 1987.
Chemical Abstracts 109: 92871e abstracting: Fahmy et al. "Synthesis of some new p–lactams . . ." Indian J. Chem., Sect. B. vol. 26(B)(9), pp. 884–7, 1987.
Chemical Abstracts 99: 158317n abstracting: Asaad et al. "New pyrazolines and pyrazoles . . ." Egypt. J. Chem. vol. 25(3), pp. 293–300, 1982.
Chemical Abstracts 94: 65583c abstracting: Latif et al. "Newer carbamates from vanillin . . ." Indian J. Chem. Sect. B, vol. 19B(4), pp. 301–4, 1980.
Pharmazie 36, H. 11 (1981), pp. 754–756; Trisubstituted Pyrazoles of Possible Antidiabetic and Antibacterial Activity.
Aust. J. Chem., 1979, 32, 1601–12; The Preparation and Spectral Properties of Some Monosubstituted 1,3,5-Triphenyl-2-Pyrazolines.
Aust. J. Chem., 1977, 30, 629–37; The Preparation and Photochemical Properties of Some 1,3-Diphenyl-2-Pyrazolines Containing a Heteroaromatic Substituent.
Can. J. Chem., 1979, 5713, 360–366; On the Syntheses and the Optical Properties of Optically Active 2-Pyrazoline Compounds.
European Search Report for EP 90 11 3022.

Primary Examiner—Allen J. Robinson
Assistant Examiner—John D. Pak
Attorney, Agent, or Firm—Sprung Horn Kramer & Woods

[57] ABSTRACT

Combating fungi with 1,3,5-triaryl-2-pyrazolines of the formula

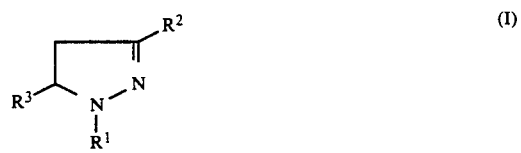

(I)

in which
R$^1$, R$^2$ and R$^3$ are optionally substituted phenyl. Those compounds in which R$^2$ is phenyl, R$^3$ is 4-hydroxyphenyl and R$^1$ is 4-chlorophenyl, 4-methylphenyl or 4-methoxyphenyl are new and especially active.

4 Claims, No Drawings

FUNGICIDAL 1,3,5-TRIARYL-2-PYRAZOLINES

The invention relates to the use of 1,3,5-triaryl-2-pyrazoline-derivatives, some of which are known, for combating pests, to new 1,3,5-triaryl-2-pyrazoline derivatives, and to a process for their preparation.

It is already known that certain 1,3,5-triaryl-2-pyrazoline derivatives are used as spasmolytic drugs or as starting substances in the preparation of pharmaceutical active substances (compare Res. Commun. Chem. Pathol. Pharmacol. 56 (1), 129–32 (1987), quoted in CA 107, 51823 f; J. Pharm. Sci. 76 (8), 626–32 (1987), quoted in CA 107, 228455 r).

The syntheses of numerous 1,3,5-triaryl-2-pyrazoline derivatives are also described (cf., inter alia, Can. J. Chem. 57 (3), 360–66 (1979); Aust. J. Chem. 32 (7), 1601–12 (1979); Pharmazie 36 (11), 754–56 (1981); Khim, Geterosikl Soedin. 7, 965–68 (1984); J. Chin. Chem. Soc. (Taipei) 31 (4), 383–90 (1984); Rev. Roum. Chim. 31 (6), 629–35 (1986)), but nothing is known about their activity in plant protection.

Furthermore, numerous 1,3,5-triaryl-2-pyrazoline derivatives are known as colorants and optical brighteners (compare, inter alia, Ukr. Khim. Zh. 45 (6), 553–56 (1979); Aust. J. Chem. 30 (3), 629–37 (1977); Nippon Kagaku Kaishi 2, 271–75 (1978); CH-609977; DE 2,749,982; DE 2,644,286; DE 2,550,548).

Moreover, it is already known that 4-(2-pyrazolin-3-yl)-phenylaminophenyl sulphides and sulphones have bactericidal properties (compare Egypt J. Pharm Sci. 27 (1–4), 43–58 (1986), quoted in CA 107, 175983c).

In addition, it has been published that certain 1,3,5-triaryl-2-pyrazoline derivatives, such as, for example, 1-(4-chlorophenyl))-3-(3,4-dichlorophenyl)-5-phenyl-2-pyrazoline, inhibit the aflatoxin production of *Aapergillus flavus* (compare Pestic. Sci. 16, 147–51 (1985)).

A bactericidal and fungicidal in-vitro activity has been described of some 1,3,5-triaryl-2-pyrazoline derivatives, such as, for example, of 1,5-diphenyl-3-(4-carboxyphenyl)-2-pyrazoline (compare Egypt. J. Pharm Sci. 25 (3), 293–300 (1982)). Nothing is known about the application of this substance in plant protection.

There is also evidence that some 1,3,5-triaryl-2-pyrazoline derivatives, such as, for example, 3,4- di-(4-fluorophenyl)-1-(4-trifluoromethoxyphenyl)carbamoyl-pyrazoline, have an insecticidal activity (compare European Patent 0,267,869).

It has been found that the 1,3,5-triaryl-2-pyrazoline derivatives, some of which are known, of the general formula (I),

in which

R$^1$, R$^2$ and R$^3$ independently of one another in each case represent phenyl which is optionally mono-substituted or polysubstituted by identical or different substituents, suitable substituents being: halogen, hydroxyl, mercapto, nitro, amino, sulpho (—SO$_3$H), straight-chain or branched alkyl having 1 to 4 carbon atoms, straight-chain or branched halogenoalkyl, halogenoalkoxy or halogenoalkylthio, each of which has 1 to 4 carbon atoms and each of which has 1 to 9 identical or different halogen atoms, straight-chain or branched alkoxy or alkylthio, each of which has 1 to 4 carbon atoms, (di)alkylamino having 1 to 4 carbon atoms in the respective straight-chain or branched alkyl moieties, carboxyl, straight-chain or branched alkoxycarbonyl having 1 to 8 carbon atoms in the alkoxy moiety, and straight-chain or branched acyloxy having 1 to 8 carbon atoms, or other suitable substituents are phenyl, phenoxy or phenoxycarbonyl, each of which is optionally monosubstituted or polysubstituted by identical or different substituents, suitable substituents being the substituents mentioned above in the case of phenyl, have fungicidal properties.

The 1,3,5-triaryl-2-pyrazoline derivatives of the formula (I) which are to be used according to the invention have an asymmetrically substituted carbon atom. The invention relates to the individual isomers as well as to the mixtures thereof.

Surprisingly, the 1,3,5-triaryl-2-pyrazoline derivatives of the formula (I) which are to be used according to the invention have a better fungicidal activity than 3,4-di-(4-fluorophenyl) -1-(4-trifluoromethoxyphenyl)-carbamoyl-pyrazoline, which is a chemically similar compound and known from the prior art.

Formula (I) provides a general definition of the 1,3,5-triaryl-2-pyrazoline derivatives which are to be used according to the invention. Preferred compounds of the formula (I) are those in which R$^1$, R$^2$ and R$^3$ independently of one another in each case represent phenyl which is optionally mono-substituted to trisubstituted by identical or different substituents, suitable substituents being: fluorine, chlorine, bromine, hydroxyl, mercapto, nitro, amino, sulpho (—SO$_3$H), straight-chain or branched alkyl having 1 to 3 carbon atoms; halogenoalkyl, halogenoalkoxy or halogenoalkylthio, each of which has 1 or 2 carbon atoms and each of which has 1 to 5 fluorine and/or chlorine atoms, straight-chain or branched alkoxy or alkylthio, each of which has 1 to 3 carbon atoms, alkylamino or dialkylamino having 1 or 2 carbon atoms in the respective alkyl moieties, carboxyl, straight-chain or branched alkoxycarbonyl having 1 to 6 carbon atoms in the alkoxy moiety, and straight-chain or branched acyloxy having 1 to 6 carbon atoms; or phenyl, phenoxy or phenoxycarbonyl, each of which is optionally monosubstituted to trisubstituted by identical or different substituents, substituents which may be mentioned being those listed as preferred in the case of phenyl.

Particularly preferred are those compounds of the formula (I) in which

R$^1$, R$^2$ and R$^3$ independently of one another in each case represent phenyl which is optionally mono-substituted or disubstituted by identical or different substituents, suitable substituents being: fluorine, chlorine, bromine, hydroxyl, mercapto, nitro, amino, sulpho (—SO$_3$H), methyl, ethyl, trifluoromethyl, trifluoromethoxy, trifluoromethylthio, methoxy, methylthio, methylamino, dimethylamino, carboxyl, methoxycarbonyl, ethoxycarbonyl, n- or i-propoxycarbonyl, n-, s-, i- or t-butoxycarbonyl, formyloxy, acetyloxy, propionyloxy, n-butyryloxy or i-butyryloxy; or phenyl, phenoxy or phenoxycarbonyl, each of which is optionally monosubstituted or disubstituted by identical or different substituents, substituents which may be mentioned being the substituents listed as particularly preferred in the case of phenyl.

Some of the 1,3,5-triaryl-2-pyrazoline derivatives of the formula (I) which are to be used according to the invention, are known:

The following 1,3,5-triaryl-2-pyrazoline derivatives were hitherto unknown.

1-(4-Chlorophenyl)-3-phenyl-5-(4-hydroxyphenyl)-2-pyrazoline, 1-(4-methylphenyl)-3-phenyl-5-(4-hydroxyphenyl)-2-pyrazoline and 1-(4-methoxyphenyl)-3-phenyl-5-(4-hydroxyphenyl)-2)pyrazoline, which are likewise part of the invention and are described by the general formula (1A)

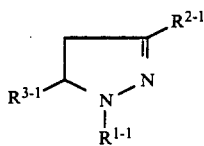

in which
R$^{1-1}$ represents 4-chlorophenyl, 4-methylphenyl or 4-methoxyphenyl,
R$^{2-1}$ represents phenyl and
R$^{3-1}$ represents 4-hydroxyphenyl.

The abovementioned compounds, new as well as known, can be synthesized by customary methods analogously to known processes (compare, inter alia, Can. J. Chem. 57 (3), 360–66 (1979); Indian J. Chem. 19 B (5), 364–67 (1980)). These new 1,3,5-triaryl-2-pyrazoline derivatives of the formula (IA) are obtained for example by condensing enones of the formula (II)

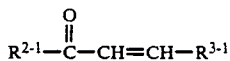

in which
R$^{2-1}$ represents phenyl and
R$^{3-1}$ represents 4-hydroxyphenyl,
with hydrazines of the formula (III)

in which
R$^{1-1}$ represents 4-chlorophenyl, 4-methylphenyl or 4-methoxyphenyl,
if appropriate in the presence of a diluent such as, for example, acetic acid, and if appropriate in the presence of a catalyst such as, for example, sulphuric acid, at temperatures between 20° C. and 150° C.

If, for example, 1-(4-chlorophenyl)-3-(4-hydroxyphenyl)-2-propen-1-one and phenylhydrazine are used as starting substances, the course of the reaction for the preparation of the new compounds may be represented by the following equation:

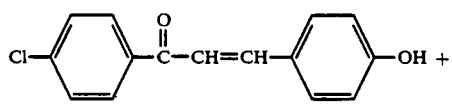

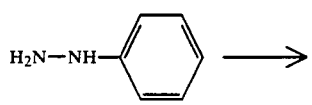

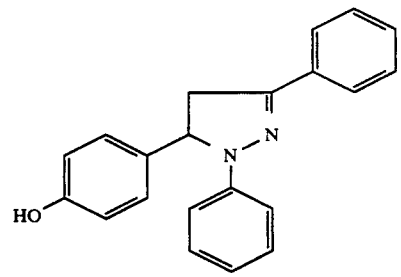

Enones of the formula (II) and hydrazines of the formula (III) are generally known compounds of organic chemistry.

The active compounds to be used according to the invention exhibit a powerful action against pests and can be employed in practice for combating undesired harmful organisms. The active compounds are suitable for use as plant protection agents and in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum*; Phytophthora species, such as, for example, *Phytophthora infestans*;

Pseudoperonospora species, such as, for example, *Pseudoperonospora humuli* or *Pseudoperonospora cubensis*;

Plasmopara species, such as, for example, *Plasmopara viticola*;

Peronospora species, such as, for example, *Peronospora pisi* or *P. brassicae*;

Erysiphe species, such as, for example, *Erysiphe graminis*;

Sphaerotheca species, such as, for example, *Sphaerotheca fuliginea*;

Podosphaera species, such as, for example, *Podosphaera leucotricha*;

Venturia species, such as, for example, *Venturia inaequalis*;

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus*;

Puccinia species, such as, for example, *Puccinia recondita*;

Tilletia species, such as, for example, *Tilletia caries*;

Ustilago species, such as, for example, *Ustilago nuda* or *Ustilago avenae*;

Pellicularia species, such as, for example, *Pellicularia sasakii*;

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds which are to be used according to the invention are particularly suitable in this case for combating mildew in barley (*Erysiphe graminis* f.sp. hordei) and for protective use against mildew in wheat (*Erysiphe graminis* f. sp. tritici).

Moreover, some of the active compounds to be used according to the invention also have a fungicidal action against *Leptosphaeria nodorum* and *Pyrenophora teres* in cereals, against mildew in cucumbers (Sphaerotneca) and grape vine (Uncinula), and against Pyricularia in rice.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, and ULV cold mist and warm mist formulations.

These formulations are produced in a known manner, for example by mixing the active compounds with extenders, that is, liquid solvents, liquefied gases under pressure and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant those liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds to be used according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of the soil, active compound concentrations of 0.00001 to 0.1% by weight, preferably 0.0001 to 0.02% by weight, are required at the place of action.

The preparation and use of the active compounds which can be used according to the invention can be seen from the examples which follow.

USE EXAMPLES

In the Use Examples which follow, the compound listed below is used as comparison substance:

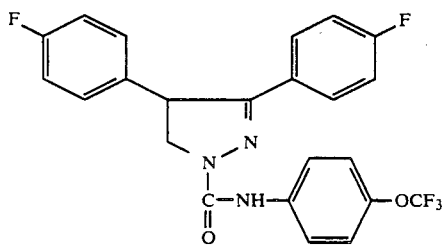

3,4-di-(4-fluorophenyl) -1-(4-trifluoromethoxyphenyl)-carbamoylpyrazoline (disclosed in European Patent 0,267,869).

EXAMPLE A

Erysiphe test (barley)/curative
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are dusted with spores of Erysiphe graminis f. sp. hordei. 48 hours after the inoculation, the plants are sprayed with the preparation of active compound until dew-moist.

The plants are placed in a greenhouse at a temperature of about 20° C. and a relative atmospheric humidity of about 80%, in order to promote the development of mildew pustules.

Evaluation is carried out 7 days after the inoculation.

In this test, a clearly superior activity compared with the prior art is shown, for example, by the compounds of the following Preparation Examples: 4, 1, 2, 3.

TABLE A

Erysiphe Test (Barley)/curative

| Active compound | Active compound concentration in the spray liquor in % by weight | Degree of effectiveness in % of the untreated control |
| --- | --- | --- |
| (A) known | 0.025 | 50 |
| (4) | 0.025 | 96 |
| (1) | 0.025 | 88 |

TABLE A-continued

| | Erysiphe Test (Barley)/curative | |
|---|---|---|
| Active compound | Active compound concentration in the spray liquor in % by weight | Degree of effectiveness in % of the untreated control |
| (2) [structure: 5-(4-hydroxyphenyl)-1-(4-chlorophenyl)-3-phenyl-4,5-dihydropyrazole] | 0.025 | 100 |
| (3) [structure: 5-(4-hydroxyphenyl)-1-(4-methylphenyl)-3-phenyl-4,5-dihydropyrazole] | 0.025 | 84 |

EXAMPLE B

Erysiphe test (wheat)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. *tritici*.

The plants are placed in a greenhouse at a temperature of about 20° C. and a relative atmospheric humidity of about 80%, in order to promote the development of mildew pustules.

Evaluation is carried out 7 days after the inoculation.

In this test, a clearly superior activity compared with the prior art is shown for example by the compounds of Preparation Examples 4 and 3.

TABLE B

| | Erysiphe Test (Wheat)/protective | |
|---|---|---|
| Active compound | Active compound concentration in the spray liquor in % by weight | Degree of effectiveness in % of the untreated control |
| (A) known [structure: 3,5-bis(4-fluorophenyl)-1-(N-(4-trifluoromethoxyphenyl)carbamoyl)-4,5-dihydropyrazole] | 0.025 | 0 |

TABLE B-continued

| Erysiphe Test (Wheat)/protective | | |
|---|---|---|
| Active compound | Active compound concentration in the spray liquor in % by weight | Degree of effectiveness in % of the untreated control |
| (4) structure: 1,3-diphenyl-5-(4-hydroxyphenyl)-N-(4-methoxyphenyl)-2-pyrazoline | 0.025 | 100 |
| (3) structure: 1,3-diphenyl-5-(4-hydroxyphenyl)-N-(4-methylphenyl)-2-pyrazoline | 0.025 | 100 |

Preparation Examples

EXAMPLE 1

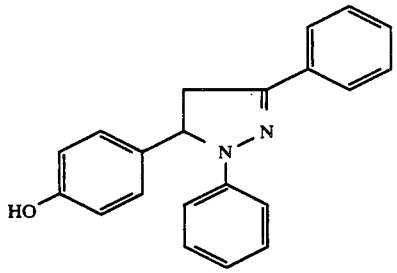

2.24 g (10.0 mMol) of 1-phenyl-3-(4-hydroxyphenyl)-2-propen-1-one are suspended in glacial acetic acid at room temperature, and the mixture is treated with 1.08 g (10.0 mMol) of phenylhydrazine. The reaction mixture is slowly heated to 100° C. and maintained at this temperature for 2 hours. The reaction product crystallizes out on cooling. For purification, the product is dissolved in 30 ml of ethyl acetate, the solution is washed with sodium hydrogen carbonate solution and then with water. After the solution has been dried over sodium sulphate, it is concentrated, whereupon the product crystallizes out. This gives 1.80 g (57% of theory) of 1,3-diphenyl-5-(4-hydroxy-phenyl)-2-pyrazoline of melting point 144° C.–145° C.

The compounds listed below in Table 1 are obtained in a corresponding manner and following the general preparation instructions.

TABLE 1

| Example No. | $R^1$ | $R^2$ | $R^3$ | Melting point |
|---|---|---|---|---|
| 2 | —⟨4-Cl-C₆H₄⟩ | —⟨C₆H₅⟩ | —⟨4-OH-C₆H₄⟩ | 174–175° C. |
| 3 | —⟨4-CH₃-C₆H₄⟩ | —⟨C₆H₅⟩ | —⟨4-OH-C₆H₄⟩ | 102–103° C. |

TABLE 1-continued

| Example No. | R¹ | R² | R³ | Melting point |
|---|---|---|---|---|
| 4 | 4-MeO-C₆H₄– | C₆H₅– | 4-HO-C₆H₄– | 171–172° C. |
| 5 | 4-Cl-C₆H₄– | 4-Cl-C₆H₄– | 4-Cl-C₆H₄– | 142–144° C. |
| 6 | C₆H₅– | 4-Cl-C₆H₄– | 4-Cl-C₆H₄– | 140–142° C. |
| 7 | 4-MeO-C₆H₄– | C₆H₅– | 4-(CH₃C(O)O)-C₆H₄– | 66–68° C. |
| 8 | 3,4-Cl₂-C₆H₃– | C₆H₅– | 4-HO-C₆H₄– | Oil |
| 9 | C₆H₅– | 4-Cl-C₆H₄– | 4-HO-C₆H₄– | 153–155° C. |
| 10 | 4-Cl-C₆H₄– | 4-Cl-C₆H₄– | 4-HO-C₆H₄– | Oil |
| 11 | C₆H₅– | 4-HO-C₆H₄– | 4-Cl-C₆H₄– | 159–160° C. |
| 12 | 4-Cl-C₆H₄– | 4-HO-C₆H₄– | 4-Cl-C₆H₄– | 126–128° C. |
| 13 | 3,4-Cl₂-C₆H₃– | 4-HO-C₆H₄– | 4-Cl-C₆H₄– | 68–70° C. |
| 14 | 3-NO₂-C₆H₄– | C₆H₅– | 4-HO-C₆H₄– | 178–180° C. |
| 15 | 3-CH₃-C₆H₄– | C₆H₅– | 4-HO-C₆H₄– | 157–158° C. |

TABLE 1-continued

| Example No. | R¹ | R² | R³ | Melting point |
|---|---|---|---|---|
| 16 | 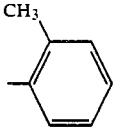 | 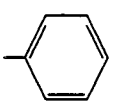 | 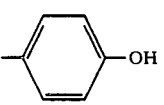 | 190–192° C. |
| 17 |  | 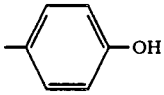 | 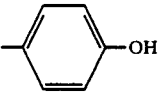 | 238–240° C. |
| 18 | 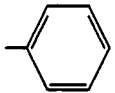 | 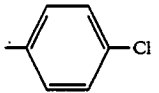 | 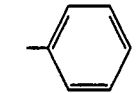 | 139–141° C. |

It is understood that the specification and examples are illustrative but not limitative of the present invention and that other embodiments within the spirit and scope of the invention will suggest themselves to those skilled in the art.

What is claimed is:

1. A method of combating fungi which comprises applying to such fungi or to a fungus habitat a fungicidally effective amount of a 1,3,5-triphenyl-2-pyrazoline of the general formula

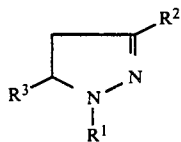

in which
R¹ is phenyl which is monosubstituted or disubstituted by identical or different substituents from the group consisting of chlorine, methyl, ethyl, and nitro,
R² is phenyl which is optionally monosubstituted by chlorine or hydroxyl and
R³ is phenyl which is monosubstituted by hydroxyl, chlorine or acetyloxy.

2. The method according to claim 1, wherein said 1,3,5-triphenyl-2-pyrazoline is applied to a plant or to a field in which a plant is growing or to be grown.

3. The method according to claim 1, wherein said 1,3,5-triphenyl-2-pyrazoline is 1-(4-chlorophenyl)-3-phenyl-5-(4-hydroxy-phenyl)-2-pyrazoline of the formula

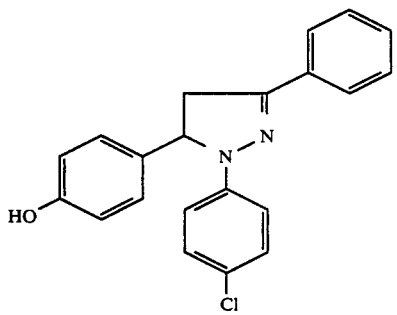

4. The method according to claim 1, wherein said 1,3,5-triphenyl-2-pyrazoline is 1-(4-methylphenyl)-3-phenyl-5-(4-hydroxy-phenyl)-2-pyrazoline of the formula

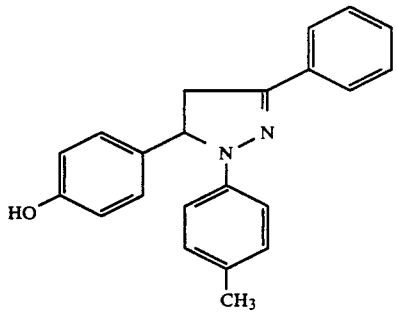

* * * * *